US008110614B2

(12) United States Patent
Ito et al.

(10) Patent No.: US 8,110,614 B2
(45) Date of Patent: Feb. 7, 2012

(54) ADAMANTANE DERIVATIVE, METHOD FOR PRODUCING THE SAME, AND RESIN COMPOSITION CONTAINING ADAMANTANE DERIVATIVE

(75) Inventors: Katsuki Ito, Chiba (JP); Yasunari Okada, Chiba (JP); Hideki Yamane, Chiba (JP); Akio Kojima, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 225 days.

(21) Appl. No.: 12/516,102

(22) PCT Filed: Nov. 21, 2007

(86) PCT No.: PCT/JP2007/072507
§ 371 (c)(1),
(2), (4) Date: May 22, 2009

(87) PCT Pub. No.: WO2008/065939
PCT Pub. Date: Jun. 5, 2008

(65) Prior Publication Data
US 2010/0056663 A1    Mar. 4, 2010

(30) Foreign Application Priority Data

Nov. 29, 2006    (JP) .................................. 2006-322044

(51) Int. Cl.
*C08F 2/46* (2006.01)
*C08F 20/10* (2006.01)
*C07C 39/04* (2006.01)
*C07C 69/52* (2006.01)
*C07D 303/00* (2006.01)
*C07D 301/27* (2006.01)
*C08G 65/08* (2006.01)

(52) U.S. Cl. ........ 522/170; 522/181; 522/182; 526/328; 528/87; 528/97; 528/106; 528/112; 549/514; 549/539; 549/543; 549/554; 560/221; 568/630; 568/632; 568/665

(58) Field of Classification Search .................. 549/554, 549/514, 539, 543; 568/665, 733, 630, 632; 560/221; 522/170, 181, 182; 528/87, 97, 528/101, 106, 112; 526/328
See application file for complete search history.

(56) References Cited

U.S. PATENT DOCUMENTS

| 6,066,711 | A | 5/2000 | Hanazawa et al. | |
|---|---|---|---|---|
| 6,228,499 | B1 * | 5/2001 | Nakauchi et al. | 428/412 |
| 6,284,185 | B1 * | 9/2001 | Tokuda et al. | 264/494 |
| 6,326,414 | B1 * | 12/2001 | Iida | 522/16 |
| 6,458,866 | B1 * | 10/2002 | Oppermann et al. | 522/174 |
| 6,534,621 | B2 * | 3/2003 | Boriack et al. | 528/87 |
| 6,959,986 | B2 * | 11/2005 | Ushirogouchi et al. | 347/100 |
| 7,754,903 | B2 * | 7/2010 | Takenaka et al. | 549/510 |
| 7,790,917 | B2 * | 9/2010 | Okada et al. | 560/194 |
| 7,803,851 | B2 * | 9/2010 | Ishibashi et al. | 523/160 |
| 7,939,682 | B2 * | 5/2011 | Okada et al. | 549/510 |
| 7,960,483 | B2 * | 6/2011 | Ito et al. | 525/524 |
| 8,017,800 | B2 * | 9/2011 | Okada et al. | 560/194 |
| 8,022,151 | B2 * | 9/2011 | Okada et al. | 525/533 |
| 2002/0016414 | A1 | 2/2002 | Lau et al. | |
| 2008/0071033 | A1 * | 3/2008 | Sugiyama | 525/326.3 |
| 2009/0099326 | A1 * | 4/2009 | Okada et al. | 526/242 |
| 2009/0137775 | A1 * | 5/2009 | Ito | 528/405 |
| 2009/0149665 | A1 * | 6/2009 | Okada et al. | 549/511 |
| 2010/0071033 | A1 * | 3/2010 | Umezawa et al. | 726/3 |

FOREIGN PATENT DOCUMENTS

| JP | 4 39665 | 2/1992 |
|---|---|---|
| JP | 6 305044 | 11/1994 |
| JP | 8 286371 | 11/1996 |
| JP | 09 302077 | 11/1997 |
| JP | 2002 341533 | 11/2002 |
| JP | 2003 530464 | 10/2003 |
| JP | 2006 307062 | 11/2006 |
| WO | 99 26612 | 6/1999 |
| WO | 2007 125890 | 11/2007 |

OTHER PUBLICATIONS

Ng, S., "Nuclear Magnetic Resonance Spectra of Adamantyl-Substituted Phenols and Solvent-Induced Shifts of Sterically Hindered Protons", J. Chem. Soc. Perkins Trans. II, No. 11, pp. 1514-1517 (1972).

Katsumi Shimada, et al., "Market development and material technologies of next-generation light source high-brightness white LED", Material Stage, vol. 3, No. 3, 2003, pp. 20-24 (with English translation).

* cited by examiner

*Primary Examiner* — Susan W Berman

(74) *Attorney, Agent, or Firm* — Oblon, Spivak, McClelland, Maier & Neustadt, L.L.P.

(57) ABSTRACT

Adamantane derivatives are provided including a phenolic hydroxyl group-containing adamantane derivative, a glycidyloxy group-containing adamantane derivative, and an adamantyl group-containing epoxy modified acrylate, which exhibit excellent transparency, light resistance, and heat resistance properties. Also provided are resin compositions containing the adamantane derivatives. Further provided are corresponding methods for producing the adamantane derivatives, as well as the resin compositions containing the same.

12 Claims, No Drawings

ADAMANTANE DERIVATIVE, METHOD FOR PRODUCING THE SAME, AND RESIN COMPOSITION CONTAINING ADAMANTANE DERIVATIVE

CROSS-REFERENCE TO RELATED APPLICATIONS

The present application is a 35 U.S.C. §371 National Stage patent application of International patent application PCT/JP2007/072507, filed on Nov. 21, 2007, which claims priority to Japanese patent application JP 2006-322044, filed on Nov. 29, 2006.

TECHNICAL FIELD

The present invention relates to a novel adamantane derivative excellent in transparency, heat resistance and mechanical properties, a production method thereof, and a resin composition containing the adamantane derivative.

BACKGROUND ART

Adamantane is a highly symmetrical and stable compound in which four cyclohexane rings are condensed to form a cage-like structure. The derivative of adamantane is known as a useful raw material for pharmaceuticals, highly functional industrial materials and the like because of its unique functions. For example, attempts to use the adamantane derivative for a substrate of an optical disk, an optical fiber, a lens, and the like are being made because the adamantane derivative has optical characteristics, heat resistance, and the like (for example, refer to Patent Documents 1 and 2). Further, attempts to use adamantane esters as a raw material for a photoresist resin are also being made by employing its acid sensitivity, resistance to dry etching, transmittance of an ultraviolet light, and the like (for example, refer to Patent Document 3).

In recent years, in the field of electronic and optical materials, investigation is progressing to enhance or improve the performance of optical and electronic parts. Examples of such investigation are improvement of fineness, widening of view angle, and improvement of image quality of a flat panel display using liquid crystal, organic electroluminescence (organic EL) and the like, increasing of brightness, shortening of wavelength, and increasing of whiteness of the light source using an optical semiconductor such as a light-emitting diode (LED) and the like, as well as increasing of frequency of electronic circuit and optical circuit and optical communication. In addition, semiconductor technology is significantly progressing and electronic devices are rapidly becoming miniaturized, light-weighted, highly performed, and multifunctionalized. In response to this trend, high density and multiple wiring are desired for interconnection substrates.

On the other hand, epoxyacrylate resins are used for various coating agents, structural materials, a solder resist for an interconnection substrate, a protection film for a color filter of a liquid crystal display and an image sensor, a color resist, and the like. As for a solder resist, a bisphenol-A type epoxyacrylate resin is disclosed (for example, refer to Patent Document 4). As for a photosensitive composition for a color filter, a cresol-novolac type epoxyacrylate resin is disclosed (for example, refer to Patent Document 5). However, the transparency, (long-term) heat resistance, and (long-term) light resistance of these epoxyacrylate resins are limited and materials satisfying those demanded characteristics are desired.

In the epoxy resins, thermosetting-type resins such as conventional bisphenol-A type epoxy resins and the like have the same problems as mentioned above and sealing materials satisfying those demanded characteristics are also desired (for example, refer to Non-patent Document 1).

In addition, as for the electronic circuit integrated with semiconductors and the like, in association with the progress of information-oriented society, information quantity and communication speed are increasing and the apparatuses are being miniaturized. Therefore, the miniaturization, integration, and increasing of frequency of the circuit are required. Furthermore, an optical circuit using an optical waveguide and the like which enables more rapid processing is also investigated. For these applications, bisphenol-A type epoxy resins, epoxyacrylate resins, and the like are conventionally used as a sealing resin, an adhesive resin or film, or a resin for lens. However, there are problems of high dielectric constant, poor heat resistance and the like in using these resins in the electronic circuit. In the optical waveguide and sealing of LED, there are problems of decreased transparency, yellowing of the resin by degradation, and the like.

Patent Document 1: Japanese Patent Laid-Open Publication No. H06-305044
Patent Document 2: Japanese Patent Laid-Open Publication No. H09-302077
Patent Document 3: Japanese Patent Laid-Open Publication No. H04-39665
Patent Document 4: Japanese Patent Laid-Open Publication No. H08-286371
Patent Document 5: Japanese Patent Laid-Open Publication No. 2002-341533
Non-patent Document 1: June issue of monthly "Material Stage", 2003, p. 20-24, Technical Information Institute Co., Ltd.

DISCLOSURE OF THE INVENTION

From the circumstances mentioned above, an object of the present invention is to provide an adamantane derivative suitable as a solder resist for an interconnection substrate, a protection film for a color filter of a liquid crystal display and a solid-state imaging element, a colored composition for a color filter, interlayer insulation film for a liquid crystal display, a sealant for an electronic circuit (a sealant for an optical semiconductor and a sealant for an organic EL element), an optoelectronic part (an optical waveguide, a lens for optical communication, an optical film, and the like), and adhesives for these devices, and others, and having optical characteristics such as transparency, (long-term) light resistance, and the like, long-term heat resistance, electric characteristics such as dielectric constant and the like, and good mechanical properties; a production method of the adamantane derivative; and a resin composition containing the above-mentioned adamantane derivative.

As a result of keen examination, the present inventors found that a resin composition which provides a cured product suitable as an optoelectronic part and the like is obtained from an adamantane derivative having a specific structure. The present invention has been completed based on this finding.

Thus, the present invention provides an adamantane derivative mentioned below, a production method thereof, and a resin composition containing the adamantane derivative.

1. An adamantane derivative represented by the general formula (I),

[Chemical formula 1]

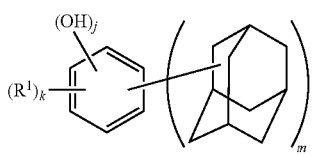
(I)

[wherein $R^1$ represents $C_nH_{2n+1}$ (n is an integer of 1 to 10); j is an integer of 1 to 4; k is an integer of 0 to 3; m is an integer of 2 to 5; and $j+k+m \leq 6$.].

2. A method for producing an adamantane derivative represented by the general formula (I), comprising reacting adamantane alcohols or adamantane halides with phenols,

[Chemical formula 2]

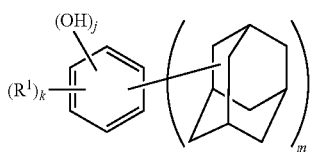
(I)

[wherein $R^1$, j, k, and m are the same as above.].

3. An adamantane derivative represented by the general formula (II),

[Chemical formula 3]

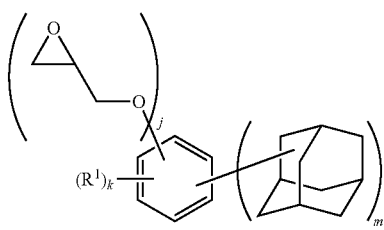
(II)

[wherein $R^1$, j, k, and m are the same as above.].

4. A method for producing an adamantane derivative represented by the general formula (II), comprising reacting an adamantane derivative represented by the general formula (I) with epichlorohydrin,

[Chemical formula 4]

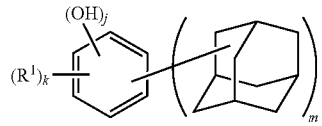
(I)

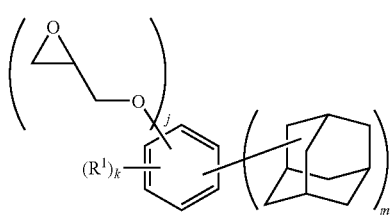
(II)

[wherein $R^1$, j, k, and m are the same as above.].

5. A resin composition containing an adamantane derivative represented by the general formula (II) and an epoxy resin curing agent,

[Chemical formula 5]

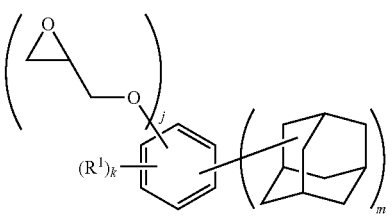
(II)

[wherein $R^1$, j, k, and m are the same as above.].

6. A cured product obtained by curing the resin composition described in the above-mentioned 5 by heating or light irradiation.

7. An adamantane derivative represented by the general formula (III),

[Chemical formula 6]

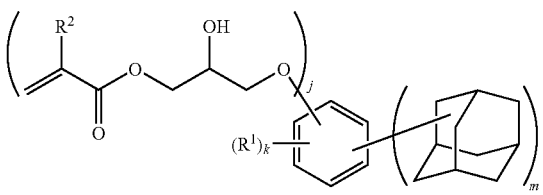
(III)

[wherein $R^1$, j, k, and m are the same as above; and $R^2$ represents H, $CH_3$, F, or $CF_3$.].

8. A method for producing an adamantane derivative represented by the general formula (III), comprising reacting an adamantane derivative represented by the general formula (II) with acrylic acids,

[Chemical formula 7]

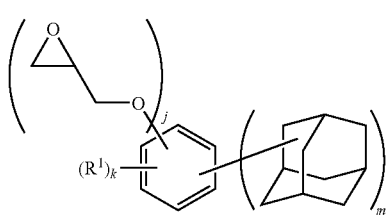
(II)

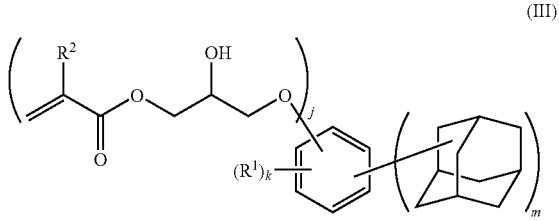

(III)

[wherein $R^1$, $R^2$, j, k, and m are the same as above.].

9. A resin composition containing an adamantane derivative represented by the general formula (III) and a thermopolymerization initiator or a photopolymerization initiator,

[Chemical formula 8]

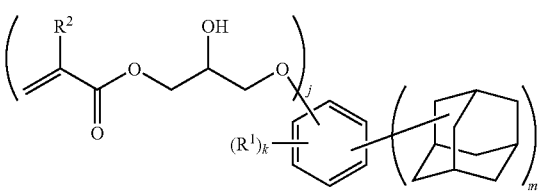

(III)

[wherein $R^1$, $R^2$, j, k, and m are the same as above.].

10. A cured product obtained by curing the resin composition described in the above-mentioned 9 by heating or light irradiation.

The adamantane derivative of the present invention provides a cured product suitable as a solder resist for an interconnection substrate, a protection film for a color filter of a liquid crystal display and an image sensor, a colored composition for a color filter, a sealant for an electronic circuit (a sealant for an optical semiconductor and a sealant for an organic EL element), an optoelectronic part (an optical waveguide, a lens for optical communication, an optical film, and the like), and adhesives for these devices, and others, and excellent in optical characteristics such as transparency, (long-term) light resistance, and the like, (long-term) heat resistance, and mechanical properties.

BEST MODE FOR CARRYING OUT THE INVENTION

The adamantane derivative of the present invention is a phenolic hydroxyl group-containing adamantane derivative represented by the following general formula (I), a glycidyloxy group-containing adamantane derivative represented by the following general formula (II), and an adamantyl group-containing epoxy modified acrylates represented by the following general formula (III).

[Chemical formula 9]

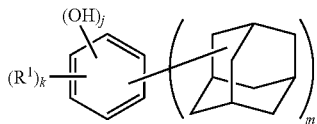

(I)

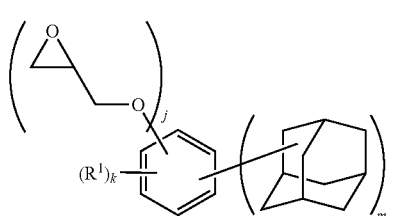

(II)

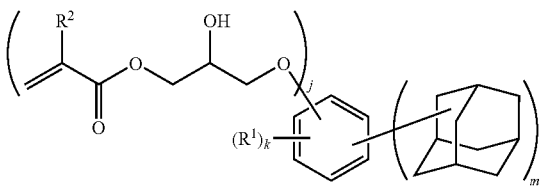

(III)

(In the formula, $R^1$ represents $C_nH_{2n+1}$ (n is an integer of 1 to 10, preferably 1 to 5); $R^2$ represents H, $CH_3$, F, or $CF_3$; j is an integer of 1 to 4, preferably 1 to 3; k is an integer of 0 to 3, preferably 0 to 2; m is an integer of 2 to 5, preferably 2 or 3; and $j+k+m \leq 6$.)

In the above-mentioned general formulae (I) to (III), examples of $R^1$ include a methyl group, an ethyl group, an n-propyl group, an iso-propyl group, an n-butyl group, an iso-butyl group, a sec-butyl group, a t-butyl group, various pentyl groups, various hexyl groups, various octyl group, and the like. When there are plural $R^1$s, they may be the same or different from each other. In the above-mentioned general formula (III), examples of the group containing $R^2$ include a (2-acryloyloxy-2-hydroxy)ethoxy group, a (2-methacryloyloxy-2-hydroxy)ethoxy group, a (2-α-fluoroacryloyloxy-2-hydroxy)ethoxy group, and a (2-α-trifluoromethylacryloyloxy-2-hydroxy)ethoxy group. When j is 2 to 4 in the above-mentioned general formula (III), they may be the same or different from each other.

The phenolic hydroxyl group-containing adamantane derivative represented by the above-mentioned general formula (I) can be obtained by reacting adamantane alcohols or adamantane halides with phenols.

Examples of the adamantane alcohols or adamantane halides as a raw material include 1-adamantanol, 1-bromoadamantane, 1,3-adamantane diol, 1,3-dibromoadamantane, 1,3,5-adamantane triol, 1,3,5-tribromoadamantane, 1,3,5,7-adamantane tetraol, 1,3,5,7-tetrabromoadamantane, 2-adamantanone, 4-hydroxy-2-adamantanone, 5-hydroxy-2-adamantanone, and the like.

The amount of these adamantane alcohols or adamantane halides to be used is usually approximately 2 to 20 moles, preferably 2 to 10 moles, per mole of the phenols. When the amount to be used is 2 moles or more per mole of the phenols, the reaction time is not too long and adequate.

Examples of the phenol include phenol, o-cresol, m-cresol, p-cresol, 4-ethyl phenol, 2,6-dimethyl phenol, 2,4-dimethyl phenol, 2,5-dimethyl phenol, 3,4-dimethyl phenol, 3,5-dimethyl phenol, 2-isopropyl phenol, 4-isopropyl phenol, 2-t-butyl phenol, 4-t-butyl phenol, 4-(1,1,3,3-tetramethylbutyl) phenol, 2,6-di-t-butyl phenol, 2,4-di-t-butyl phenol, 5-isopropyl-2-methyl phenol, 1-methyl-3-hydroxy-4-isopropyl benzene, 2,6-di-t-butyl-4-methyl phenol, 2-t-butyl-4-methyl phenol, 2,3,5-trimethyl phenol, resorcinol, catechol, hydroquinone, 4-hexyl resorcinol, 2,5-dimethyl resorcinol, 2,6-dihydrotoluene, 3,5-dihydroxytoluene, 3,5-di-t-butyl catechol, 4-methyl pyrocatechol, 4-t-butyl pyrocatechol, 2-methyl hydroquinone, t-butyl hydroquinone, 2,5-di-t-butyl hydroquinone, pyrogallol, 1,3,5-benzene triol, hydroxyquinone and the like.

The reaction of adamantane alcohols or adamantane halides and phenols is usually carried out in the presence of an acid catalyst. Examples of the acid catalyst include hydrochloric acid, sulfuric acid, p-toluenesulfonic acid, thioacetic acid, β-mercaptopropionic acid and the like. The amount of this acid catalyst to be used is usually approximately 0.01 to 1 mole, preferably 0.05 to 0.8 mole per mole of the functional group of the adamantane alcohols or adamantane halides as a raw material. When the amount of the acid catalyst to be used is 0.01 mole or more per mole of the functional group, the reaction time is not too long and adequate. When the amount of the acid catalyst to be used is 1 mole or less per mole of the functional group, the balance of the attained effect and economic efficiency is good.

In the reaction, a solvent may be used as needed. Specific examples of the solvent include cyclohexane, heptane, octane, decane, toluene, DMF (dimethylformamide), DMAc (N,N-dimethylacetamide), DMSO (dimethylsulfoxide), ethyl acetate, diethyl ether, tetrahydrofuran, dimethoxyethane, methanol, ethanol, isopropyl alcohol, acetic acid, propionic acid and the like. These solvents may be used alone or in combination of two or more kinds.

The reaction of the adamantane alcohols or adamantane halides and phenols is usually carried out at a temperature of approximately 0 to 200° C., preferably 50 to 150° C. When the reaction temperature is 0° C. or higher, the reaction rate is not lowered and adequate, therefore the reaction time is shortened. When the reaction temperature is 200° C. or lower, discoloration of the product is suppressed. The reaction pressure is approximately 0.01 to 10 MPa, preferably normal pressure to 1 MPa, in absolute pressure. When the pressure is 10 MPa or less, the safety is secured and special equipment is not required, therefore this method is industrially useful. The reaction time is usually approximately 1 minute to 24 hours, desirably 1 to 10 hours.

Examples of the phenolic hydroxyl group-containing adamantane derivative represented by the above-mentioned general formula (I) thus obtained include 2,3-bis(1-adamantyl)phenol, 2,4-bis(1-adamantyl)phenol, 2,5-bis(1-adamantyl)phenol, 2,6-bis(1-adamantyl)phenol, 3,5-bis(1-adamantyl)phenol, 2,4,6-tris(1-adamantyl)phenol, 2,3,4-tris(1-adamantyl)phenol, 2,4,5-tris(1-adamantyl)phenol, 3,4,5-tris(1-adamantyl)phenol, 2,3,5,6-tetrakis(1-adamantyl)phenol, 3,4,5,6-tetrakis(1-adamantyl)phenol, 2,3,4,5,6-pentakis(1-adamantyl)phenol, 3,4-bis(1-adamantyl)-2-methylphenol, 3,5-bis(1-adamantyl)-2-methylphenol, 3,6-bis(1-adamantyl)-2-methylphenol, 4,5-bis(1-adamantyl)-2-methylphenol, 4,6-bis(1-adamantyl)-2-methylphenol, 5,6-bis(1-adamantyl)-2-methylphenol, 3,4,5-tris(1-adamantyl)-2-methylphenol, 3,4,6-tris(1-adamantyl)-2-methylphenol, 4,5,6-tris(1-adamantyl)-2-methylphenol, 3,4,5,6-tetrakis(1-adamantyl)-2-methylphenol, 2,4-bis(1-adamantyl)-3-methylphenol, 2,5-bis(1-adamantyl)-3-methylphenol, 2,6-bis(1-adamantyl)-3-methylphenol, 4,5-bis(1-adamantyl)-3-methylphenol, 4,6-bis(1-adamantyl)-3-methylphenol, 5,6-bis(1-adamantyl)-3-methylphenol, 2,4,6-tris(1-adamantyl)-3-methylphenol, 2,5,6-tris(1-adamantyl)-3-methylphenol, 4,5,6-tris(1-adamantyl)-3-methylphenol, 2,4,5,6-tetrakis(1-adamantyl)-3-methylphenol, 2,3-bis(1-adamantyl)-4-methylphenol, 2,5-bis(1-adamantyl)-4-methylphenol, 2,6-bis(1-adamantyl)-4-methylphenol, 3,5-bis(1-adamantyl)-4-methylphenol, 2,3,6-tris(1-adamantyl)-4-methylphenol, 2,3,5-tris(1-adamantyl)-4-methylphenol, 2,3,5,6-tetrakis(1-adamantyl)-4-methylphenol, 2,3-bis(1-adamantyl)-4-ethylphenol, 2,5-bis(1-adamantyl)-4-ethylphenol, 2,6-bis(1-adamantyl)-4-ethylphenol, 3,5-bis(1-adamantyl)-4-ethylphenol, 2,3,6-tris(1-adamantyl)-4-ethylphenol, 2,3,5-tris(1-adamantyl)-4-ethylphenol, 2,3,5,6-tetrakis(1-adamantyl)-4-ethylphenol, 3,4-bis(1-adamantyl)-2,6-dimethylphenol, 3,5-bis(1-adamantyl)-2,6-dimethylphenol, 3,4,5-tris(1-adamantyl)-2,6-dimethylphenol, 3,5-bis(1-adamantyl)-2,4-dimethylphenol, 3,6-bis(1-adamantyl)-2,4-dimethylphenol, 5,6-bis(1-adamantyl)-2,4-dimethylphenol, 3,5,6-tris(1-adamantyl)-2,4-dimethylphenol, 3,4-bis(1-adamantyl)-2,5-dimethylphenol, 3,6-bis(1-adamantyl)-2,5-dimethylphenol, 4,6-bis(1-adamantyl)-2,5-dimethylphenol, 3,4,6-tris(1-adamantyl)-2,5-dimethylphenol, 2,5-bis(1-adamantyl)-3,4-dimethylphenol, 2,6-bis(1-adamantyl)-3,4-dimethylphenol, 5,6-bis(1-adamantyl)-3,4-dimethylphenol, 2,5,6-tris(1-adamantyl)-3,4-dimethylphenol, 2,4-bis(1-adamantyl)-3,5-dimethylphenol, 2,6-bis(1-adamantyl)-3,5-dimethylphenol, 2,4,6-tris(1-adamantyl)-3,5-dimethylphenol, 3,4-bis(1-adamantyl)-2-isopropylphenol, 3,5-bis(1-adamantyl)-2-isopropylphenol, 3,6-bis(1-adamantyl)-2-isopropylphenol, 4,5-bis(1-adamantyl)-2-isopropylphenol, 4,6-bis(1-adamantyl)-2-isopropylphenol, 5,6-bis(1-adamantyl)-2-isopropylphenol, 3,4,5-tris(1-adamantyl)-2-isopropylphenol, 3,4,6-tris(1-adamantyl)-2-isopropylphenol, 4,5,6-tris(1-adamantyl)-2-isopropylphenol, 3,4,5,6-tetrakis(1-adamantyl)-2-isopropylphenol, 2,3-bis(1-adamantyl)-4-isopropylphenol, 2,5-bis(1-adamantyl)-4-isopropylphenol, 2,6-bis(1-adamantyl)-4-isopropylphenol, 3,5-bis(1-adamantyl)-4-isopropylphenol, 2,3,6-tris(1-adamantyl)-4-isopropylphenol, 2,3,5-tris(1-adamantyl)-4-isopropylphenol, 2,3,5,6-tetrakis(1-adamantyl)-4-isopropylphenol, 3,4-bis(1-adamantyl)-2-t-butylphenol, 3,5-bis(1-adamantyl)-2-t-butylphenol, 3,6-bis(1-adamantyl)-2-t-butylphenol, 4,5-bis(1-adamantyl)-2-t-butylphenol, 4,6-bis(1-adamantyl)-2-t-butylphenol, 5,6-bis(1-adamantyl)-2-t-butylphenol, 3,4,5-tris(1-adamantyl)-2-t-butylphenol, 3,4,6-tris(1-adamantyl)-2-t-butylphenol, 4,5,6-tris(1-adamantyl)-2-t-butylphenol, 3,4,5,6-tetrakis(1-adamantyl)-2-t-butylphenol, 2,3-bis(1-adamantyl)-4-t-butylphenol, 2,5-bis(1-adamantyl)-4-t-butylphenol, 2,6-bis(1-adamantyl)-4-t-butylphenol, 3,5-bis(1-adamantyl)-4-t-butylphenol, 2,3,6-tris(1-adamantyl)-4-t-butylphenol, 2,3,5-tris(1-adamantyl)-4-t-butylphenol, 2,3,5,6-tetrakis(1-adamantyl)-4-t-butylphenol, 2,3-bis(1-adamantyl)-4-(1,1,3,3-tetramethylbutyl)phenol, 2,5-bis(1-adamantyl)-4-(1,1,3,3-tetramethylbutyl)phenol, 2,6-bis(1-adamantyl)-4-(1,1,3,3-tetramethylbutyl)phenol, 3,5-bis(1-adamantyl)-4-(1,1,3,3-tetramethylbutyl)phenol, 2,3,5-tris(1-adamantyl)-4-(1,1,3,3-tetramethylbutyl)phenol, 2,3,6-tris(1-adamantyl)-4-(1,1,3,3-tetramethylbutyl)phenol, 2,3,5,6-tetrakis(1-adamantyl)-4-(1,1,3,3-tetramethylbutyl)phenol, 3,4-bis(1-adamantyl)-2,6-di-t-butylphenol, 3,5-bis(1-adamantyl)-2,6-di-t-butylphenol, 3,4,5-tris(1-adamantyl)-2,6-di-t-butylphenol, 3,5-bis(1-adamantyl)-2,4-di-t-butylphenol, 3,6-bis(1-adamantyl)-2,4-di-t-butylphenol, 5,6-bis(1-adamantyl)-2,4-di-t-butylphenol, 3,5,6-tris(1-adamantyl)-2,4-di-t-butylphenol, 3,4-bis(1-adamantyl)-5-isopropyl-2-methylphenol, 3,6-bis(1-adamantyl)-5-isopropyl-2-methylphenol, 4,6-bis(1-adamantyl)-5-isopropyl-2-methylphenol, 3,4,6-tris(1-adamantyl)-5-isopropyl-2-methylphenol, 3,4-bis(1-adamantyl)-5-methyl-2-isopropylphenol, 3,6-bis(1-adamantyl)-5-methyl-2-isopropylphenol, 4,6-bis(1-adamantyl)-5-methyl-2-isopropylphenol, 3,4,6-tris(1-adamantyl)-5-methyl-2-isopropylphenol, 3,5-bis(1-adamantyl)-2,6-di-t-butyl-4-methylphenol, 3,5-bis(1-adamantyl)-2-t-butyl-4-methylphenol, 3,6-bis(1-adamantyl)-2-t-butyl-4-methylphenol, 5,6-bis(1-adamantyl)-2-t-butyl-4-methylphenol, 3,5,6-tris(1-adamantyl)-2-t-butyl-4-methylphenol, 4,6-bis(1-adamantyl)-2,3,5-trimethylphenol, 2,4-bis(1-adamantyl)-1,3-benzenediol, 2,5-bis(1-adamantyl)-1,3-benzenediol, 4,6-bis(1-adamantyl)-1,3-benzenediol, 4,5-bis(1-adamantyl)-1,3-benzenediol, 2,4,5-tris(1-adamantyl)-1,3-benzenediol, 2,4,6-tris(1-adamantyl)-1,3-benzenediol, 4,5,6-tris(1-adamantyl)-1,3-benzenediol, 2,4,5,6-tetrakis(1-adamantyl)-1,3-benzenediol, 3,4-bis(1-adamantyl)-1,2-benzenediol, 3,5-bis(1-adamantyl)-1,2-benzenediol, 3,6-bis(1-adamantyl)-1,2-benzenediol, 4,5-bis(1-adamantyl)-1,2-benzenediol, 3,4,5-tris(1-adamantyl)-1,2-benzenediol, 3,4,5,6-tetrakis(1-adamantyl)-1,2-benzenediol, 2,3-bis(1-adamantyl)-1,4-benzenediol, 2,5-bis(1-adamantyl)-1,4-benzenediol, 2,6-bis(1-adamantyl)-1,4-benzenediol, 2,3,5-tris(1-adamantyl)-1,4-benzenediol, 2,3,5,6-tetrakis(1-adamantyl)-1,4-benzenediol, 2,5-bis(1-adamantyl)-4-hexyl-1,3-benzenediol, 2,6-bis(1-adamantyl)-4-hexyl-1,3-benzenediol, 5,6-bis(1-adamantyl)-4-hexyl-1,3-benzenediol, 2,5,6-tris(1-adamantyl)-4-hexyl-1,3-benzenediol, 4,6-bis(1-adamantyl)-2,5-dimethyl-1,3-benzenediol, 4,5-bis(1-adamantyl)-2-methyl-1,3-benzenediol, 4,6-bis(1-adamantyl)-2-methyl-1,3-benzenediol, 4,5,6-tris(1-adamantyl)-2-methyl-1,3-benzenediol, 2,4-bis(1-adamantyl)-5-methyl-1,3-benzenediol, 4,6-bis(1-adamantyl)-5-methyl-1,3-benzenediol, 2,4-bis(1-adamantyl)-5-methyl-1,3-benzenediol, 4,6-bis(1-adamantyl)-3,5-di-t-butyl-1,2-benzenediol, 3,5-bis(1-adamantyl)-4-methyl-1,2-benzenediol, 3,6-bis(1-adamantyl)-4-methyl-1,2-benzenediol, 5,6-bis(1-adamantyl)-4-methyl-1,2-benzenediol, 3,5,6-tris(1-adamantyl)-4-methyl-1,2-benzenediol, 3,5-bis(1-adamantyl)-4-t-butyl-1,2-benzenediol, 3,6-bis(1-adamantyl)-4-t-butyl-1,2-benzenediol, 5,6-bis(1-adamantyl)-4-t-butyl-1,2-benzenediol, 3,5,6-tris(1-adamantyl)-4-t-butyl-1,2-benzenediol, 3,5-bis(1-adamantyl)-2-methyl-1,4-benzenediol, 3,6-bis(1-adamantyl)-2-methyl-1,4-benzenediol, 3,5,6-tris(1-adamantyl)-2-methyl-1,4-benzenediol, 3,5-bis(1-adamantyl)-2-t-butyl-1,4-benzenediol, 3,6-bis(1-adamantyl)-2-t-butyl-1,4-benzenediol, 3,5,6-tris(1-adamantyl)-2-t-butyl-1,4-benzenediol, 3,6-bis(1-adamantyl)-2,5-t-butyl-1,4-benzenediol, 4,5-bis(1-adamantyl)-1,2,3-benzenetriol, 4,6-bis(1-adamantyl)-1,2,3-benzenetriol, 4,5,6-tris(1-adamantyl)-1,2,3-benzenetriol, 2,5-bis(1-adamantyl)-1,3,4-benzenetriol, 2,6-bis(1-adamantyl)-1,3,4-benzenetriol, 5,6-bis(1-adamantyl)-1,3,4-benzenetriol, 2,5,6-tris(1-adamantyl)-1,3,4-benzenetriol and the like.

The glycidyloxy group-containing adamantane derivative represented by the above-mentioned general formula (II) can be obtained by reacting the phenolic hydroxyl group-containing adamantane derivative represented by the above-mentioned general formula (I) with epichlorohydrin. In the reaction with epichlorohydrin, the above-mentioned phenolic hydroxyl group-containing adamantane derivative may be used alone or in a mixture of two or more kinds.

The reaction of the above-mentioned phenolic hydroxyl group-containing adamantane derivative and epichlorohydrin is usually carried out in the presence of a basic catalyst. Examples of the basic catalyst include sodium amide, triethylamine, tributylamine, trioctylamine, pyridine, N,N-dimethylaniline, 1,5-diazabicyclo[4,3,0]nonene-5 (DBN), 1,8-diazabicyclo[5,4,0]undecene-7 (DBU), sodium hydroxide, potassium hydroxide, sodium hydride, sodium phosphate, potassium phosphate, sodium carbonate, potassium carbonate, silver oxide, sodium methoxide, potassium t-butoxide and the like.

The ratio of the basic catalyst to be used to the phenolic hydroxyl group-containing adamantane derivative represented by the general formula (I) as a raw material for the reaction is selected so that the molar ratio of the basic catalyst to the active hydrogen of the monomer as a raw material is approximately 0.8 to 10, preferably 1 to 5.

In the above-mentioned reaction, a quarternary ammonium salt such as tetramethylammonium chloride, tetraethylammonium chloride, tetraethylammonium bromide and the like may be added as a phase transfer catalyst. The ratio of the quarternary ammonium salt to be used is approximately 0.01 to 20 mol %, preferably 0.1 to 10 mol % to the phenolic hydroxyl group-containing adamantane derivative.

The reaction is carried out in the absence or in the presence of a solvent. The solvent is advantageously selected so that the solubility of the above-mentioned phenolic hydroxyl group-containing adamantane derivative is 0.5 mass % or more, desirably 5 mass % or more. The amount of the solvent to be used is selected so that the concentration of the above-mentioned phenolic hydroxyl group-containing adamantane derivative is 0.5 mass % or more, desirably 5 mass % or more. In this reaction, although the above-mentioned phenolic hydroxyl group-containing adamantane derivative may be reacted in a suspended state, it is desirable that the derivative is dissolved in the solvent. Specific examples of the solvent include hexane, heptane, toluene, DMF (dimethylformamide), DMAc (N,N-dimethylacetamide), DMSO (dimethylsulfoxide), ethyl acetate, diethyl ether, THF (tetrahydrofuran), acetone, methyl ethyl ketone, MIBK (methyl isobutyl ketone) and the like. These solvents may be used alone or in combination of two or more kinds.

The reaction of the phenolic hydroxyl group-containing adamantane derivative and epichlorohydrin is usually carried out at a temperature of approximately 0 to 200° C., preferably 20 to 150° C. When the reaction temperature is 0° C. or higher, the reaction rate is not lowered and adequate, therefore the reaction time is shortened. When the reaction temperature is 200° C. or lower, discoloration of the product is suppressed. The reaction pressure is approximately 0.01 to 10 MPa, preferably normal pressure to 1 MPa, in absolute pressure. When the pressure is 10 MPa or less, the safety is secured and special equipment is not required, therefore this method is industrially useful. The reaction time is usually approximately 1 minute to 24 hours, desirably 1 to 10 hours.

Usually, a compound containing a group having an epoxy ring contains an oligomer component of dimer or multimer. Therefore, in the above-mentioned reaction, an oligomer, that is, a dimer or multimer, of the glycidyloxy group-containing adamantane derivative is formed. Although the presence of these oligomers does not cause any problem, the product is purified by distillation, crystallization, column separation, and the like, as needed. The method of purification may be selected according to the characteristics of the reaction product and the kind of the impurities.

In the above-mentioned reaction, when the production of the glycidyloxy group in the glycidyloxy group-containing adamantane derivative is not sufficient, the amount of the glycidyloxy group may be improved by a ring closing reaction using a basic catalyst.

This ring closing reaction is usually carried out at a temperature of approximately 20 to 200° C., desirably 30 to 150° C. The reaction pressure is approximately 0.01 to 10 MPa, desirably normal pressure to 1 MPa, in absolute pressure. When the pressure is 10 MPa or less, the safety is secured and special equipment is not required, therefore this reaction is industrially useful. The reaction time is usually approximately 1 minute to 24 hours, desirably 30 minutes to 10 hours.

Examples of the basic catalyst include sodium hydroxide, potassium hydroxide, sodium phosphate, potassium phosphate, sodium carbonate, potassium carbonate, calcium hydroxide, magnesium hydroxide and the like.

The amount of the basic catalyst to be used is approximately 0.1 to 20 mass %, preferably 1 to 10 mass %, relative to the glycidyloxy group-containing adamantane derivative represented by the above-mentioned general formula (II). When the amount of the basic catalyst to be used is 0.1 mass % or more, the reaction rate is not lowered and adequate, therefore the reaction time is shortened. When the amount of the basic catalyst to be used is 20 mass % or less, the balance of the attained effect and economic efficiency is good.

The reaction may be carried out in the absence or in the presence of a solvent. The solvent is advantageously selected so that the solubility of the glycidyloxy group-containing adamantane derivative represented by the general formula (II) is 0.5 mass % or more, desirably 5 mass % or more. The amount of the solvent to be used is selected so that the concentration of the above-mentioned glycidyloxy group-containing adamantane derivative is 0.5 mass % or more, desirably 5 mass % or more. In this reaction, although the above-mentioned glycidyloxy group-containing adamantane derivative may be reacted in a suspended state, it is desirable that the derivative is dissolved in the solvent. Specific examples of the solvent include hexane, heptane, toluene, DMF (dimethylformamide), DMAc (N,N-dimethylacetamide), DMSO (dimethylsulfoxide), ethyl acetate, diethyl ether, tetrahydrofuran, acetone, MEK (methyl ethyl ketone), MIBK (methyl isobutyl ketone) and the like. These solvents may be used alone or in combination of two or more kinds.

The reaction product is purified by distillation, crystallization, column separation, and the like. The method of purification may be selected according to the characteristics of the reaction product and the kind of the impurities.

Examples of the glycidyloxy group-containing adamantane derivative represented by the above-mentioned general formula (II) thus obtained include 2,3-bis(1-adamantyl)glycidyloxybenzene, 2,4-bis(1-adamantyl)glycidyloxybenzene, 2,5-bis(1-adamantyl)glycidyloxybenzene, 2,6-bis(1-adamantyl)glycidyloxybenzene, 3,5-bis(1-adamantyl)glycidyloxybenzene, 2,4,6-tris(1-adamantyl)glycidyloxybenzene, 2,3,4-tris(1-adamantyl)glycidyloxybenzene, 2,4,5-tris(1-adamantyl)glycidyloxybenzene, 3,4,5-tris(1-adamantyl)glycidyloxybenzene, 2,3,5,6-tetrakis(1-adamantyl)glycidyloxybenzene, 3,4,5,6-tetrakis(1-adamantyl)glycidyloxybenzene, 2,3,4,5,6-pentakis(1-adamantyl)glycidyloxybenzene, 3,4-bis(1-adamantyl)-2-methyl-glycidyloxybenzene, 3,5-bis(1-adamantyl)-2-methyl-glycidyloxybenzene, 3,6-bis(1-adamantyl)-2-methyl-glycidyloxybenzene, 4,5-bis(1-adamantyl)-2-methyl-glycidyloxybenzene, 4,6-bis(1-adamantyl)-2-methyl-glycidyloxybenzene, 5,6-bis(1-adamantyl)-2-methyl-glycidyloxybenzene, 3,4,5-tris(1-adamantyl)-2-methyl-glycidyloxybenzene, 3,4,6-tris(1-adamantyl)-2-methyl-glycidyloxybenzene, 4,5,6-tris(1-adamantyl)-2-methyl-glycidyloxybenzene, 3,4,5,6-tetrakis(1-adamantyl)-2-methyl-glycidyloxybenzene, 2,4-bis(1-adamantyl)-3-methyl-glycidyloxybenzene, 2,5-bis(1-adamantyl)-3-methyl-glycidyloxybenzene, 2,6-bis(1-adamantyl)-3-methyl-glycidyloxybenzene, 4,5-bis(1-adamantyl)-3-methyl-glycidyloxybenzene, 4,6-bis(1-adamantyl)-3-methyl-glycidyloxybenzene, 5,6-bis(1-adamantyl)-3-methyl-glycidyloxybenzene, 2,4,6-tris(1-adamantyl)-3-methyl-glycidyloxybenzene, 2,5,6-tris(1-adamantyl)-3-methyl-glycidyloxybenzene, 4,5,6-tris(1-adamantyl)-3-methyl-glycidyloxybenzene, 2,4,5,6-tetrakis(1-adamantyl)-3-methyl-glycidyloxybenzene, 2,3-bis(1-adamantyl)-4-methyl-glycidyloxybenzene, 2,5-bis(1-adamantyl)-4-methyl-glycidyloxybenzene, 2,6-bis(1-adamantyl)-4-methyl-glycidyloxybenzene, 3,5-bis(1-adamantyl)-4-methyl-glycidyloxybenzene, 2,3,6-tris(1-adamantyl)-4-methyl-glycidyloxybenzene, 2,3,5-tris(1-adamantyl)-4-methyl-glycidyloxybenzene, 2,3,5,6-tetrakis(1-adamantyl)-4-methyl-glycidyloxybenzene, 2,3-bis(1-adamantyl)-4-ethyl-glycidyloxybenzene, 2,5-bis(1-adamantyl)-4-ethyl-glycidyloxybenzene, 2,6-bis(1-adamantyl)-4-ethyl-glycidyloxybenzene, 3,5-bis(1-adamantyl)-4-ethyl-glycidyloxybenzene, 2,3,6-tris(1-adamantyl)-4-ethyl-glycidyloxybenzene, 2,3,5-tris(1-adamantyl)-4-ethyl-glycidyloxybenzene, 2,3,5,6-tetrakis(1-adamantyl)-4-ethyl-glycidyloxybenzene, 3,4-bis(1-adamantyl)-2,6-dimethyl-glycidyloxybenzene, 3,5-bis(1-adamantyl)-2,6-dimethyl-glycidyloxybenzene, 3,4,5-tris(1-adamantyl)-2,6-dimethyl-glycidyloxybenzene, 3,5-bis(1-adamantyl)-2,4-dimethyl-glycidyloxybenzene, 3,6-bis(1-adamantyl)-2,4-dimethyl-glycidyloxybenzene, 5,6-bis(1-adamantyl)-2,4-dimethyl-glycidyloxybenzene, 3,5,6-tris(1-adamantyl)-2,4-dimethyl-glycidyloxybenzene, 3,4-bis(1-adamantyl)-2,5-dimethyl-glycidyloxybenzene, 3,6-bis(1-adamantyl)-2,5-dimethyl-glycidyloxybenzene, 4,6-bis(1-adamantyl)-2,5-dimethyl-glycidyloxybenzene, 3,4,6-tris(1-adamantyl)-2,5-dimethyl-glycidyloxybenzene, 2,5-bis(1-adamantyl)-3,4-dimethyl-glycidyloxybenzene, 2,6-bis(1-adamantyl)-3,4-dimethyl-glycidyloxybenzene, 5,6-bis(1-adamantyl)-3,4-dimethyl-glycidyloxybenzene, 2,5,6-tris(1-adamantyl)-3,4-dimethyl-glycidyloxybenzene, 2,4-bis(1-adamantyl)-3,5-dimethyl-glycidyloxybenzene, 2,6-bis(1-adamantyl)-3,5-dimethyl-glycidyloxybenzene, 2,4,6-tris(1-adamantyl)-3,5-dimethyl-glycidyloxybenzene, 3,4-bis(1-adamantyl)-2-isopropyl-glycidyloxybenzene, 3,5-bis(1-adamantyl)-2-isopropyl-glycidyloxybenzene, 3,6-bis(1-adamantyl)-2-isopropyl-glycidyloxybenzene, 4,5-bis(1-adamantyl)-2-isopropyl-glycidyloxybenzene, 4,6-bis(1-adamantyl)-2-isopropyl-glycidyloxybenzene, 5,6-bis(1-adamantyl)-2-isopropyl-glycidyloxybenzene, 3,4,5-tris(1-adamantyl)-2-isopropyl-glycidyloxybenzene, 3,4,6-tris(1-adamantyl)-2-isopropyl-glycidyloxybenzene, 4,5,6-tris(1-adamantyl)-2-isopropyl-glycidyloxybenzene, 3,4,5,6-tetrakis(1-adamantyl)-2-isopropyl-glycidyloxybenzene, 2,3-bis(1-adamantyl)-4-isopropyl-glycidyloxybenzene, 2,5-bis(1-adamantyl)-4-isopropyl-glycidyloxybenzene, 2,6-bis(1-adamantyl)-4-isopropyl-glycidyloxybenzene, 3,5-bis(1-adamantyl)-4-isopropyl-glycidyloxybenzene, 2,3,6-tris(1-adamantyl)-4-isopropyl-glycidyloxybenzene, 2,3,5-tris(1-adamantyl)-4-isopropyl-glycidyloxybenzene, 2,3,5,6-tetrakis(1-adamantyl)-4-isopropyl-glycidyloxybenzene, 3,4-bis(1-adamantyl)-2-t-butyl-glycidyloxybenzene, 3,5-bis(1-adamantyl)-2-t-butyl-glycidyloxybenzene, 3,6-bis(1-adamantyl)-2-t-butyl-glycidyloxybenzene, 4,5-bis(1-adamantyl)-2-t-butyl-glycidyloxybenzene, 4,6-bis(1-adamantyl)-2-t-butyl-glycidyloxybenzene, 5,6-bis(1-adamantyl)-2-t-butyl-glycidyloxybenzene, 3,4,5-tris(1-adamantyl)-2-t-butyl-glycidyloxybenzene, 3,4,6-tris(1-adamantyl)-2-t-butyl-glycidyloxybenzene, 4,5,6-tris(1-adamantyl)-2-t-butyl-glycidyloxybenzene, 3,4,5,6-tetrakis(1-adamantyl)-2-t-butyl-glycidyloxybenzene, 2,3-bis(1-adamantyl)-4-t-butyl-glycidyloxybenzene, 2,5-bis(1-adamantyl)-4-t-butyl-glycidyloxybenzene, 2,6-bis(1-adamantyl)-4-t-butyl-glycidyloxybenzene, 3,5-bis(1-adamantyl)-4-t-butyl-glycidyloxybenzene, 2,3,6-tris(1- adamantyl)-4-t-butyl-glycidyloxybenzene, 2,3,5-tris(1-adamantyl)-4-t-butyl-glycidyloxybenzene, 2,3,5,6-tetrakis(1-adamantyl)-4-t-butyl-glycidyloxybenzene, 2,3-bis(1-adamantyl)-4-(1,1,3,3-tetramethylbutyl)glycidyloxybenzene, 2,5-bis(1-adamantyl)-4-(1,1,3,3-tetramethylbutyl)glycidyloxybenzene, 2,6-bis(1-adamantyl)-4-(1,1,3,3-tetramethylbutyl)glycidyloxybenzene, 3,5-bis(1-adamantyl)-4-(1,1,3,3-tetramethylbutyl)glycidyloxybenzene, 2,3,5-tris(1-adamantyl)-4-(1,1,3,3-tetramethylbutyl)glycidyloxybenzene, 2,3,6-tris(1-adamantyl)-4-(1,1,3,3-tetramethylbutyl)glycidyloxybenzene, 2,3,5,6-tetrakis(1-adamantyl)-4-(1,1,3,3-tetramethylbutyl)glycidyloxybenzene, 3,4-bis(1-adamantyl)-2,6-di-t-butyl-glycidyloxybenzene, 3,5-bis(1-adamantyl)-2,6-di-t-butyl-glycidyloxybenzene, 3,4,5-tris(1-adamantyl)-2,6-di-t-butyl-glycidyloxybenzene, 3,5-bis(1-adamantyl)-2,4-di-t-butyl-glycidyloxybenzene, 3,6-bis(1-adamantyl)-2,4-di-t-butyl-glycidyloxybenzene, 5,6-bis(1-adamantyl)-2,4-di-t-butyl-glycidyloxybenzene, 3,5,6-tris(1-adamantyl)-2,4-di-t-butyl-glycidyloxybenzene, 3,4-bis(1-adamantyl)-5-isopropyl-2-methyl-glycidyloxybenzene, 3,6-bis(1-adamantyl)-5-isopropyl-2-methyl-glycidyloxybenzene, 4,6-bis(1-adamantyl)-5-isopropyl-2-methyl-glycidyloxybenzene, 3,4,6-tris(1-adamantyl)-5-isopropyl-2-methyl-glycidyloxybenzene, 3,4-bis(1-adamantyl)-5-methyl-2-isopropyl-glycidyloxybenzene, 3,6-bis(1-adamantyl)-5-methyl-2-isopropyl-glycidyloxybenzene, 4,6-bis(1-adamantyl)-5-methyl-2-isopropyl-glycidyloxybenzene, 3,4,6-tris(1-adamantyl)-5-methyl-2-isopropyl-glycidyloxybenzene, 3,5-bis(1-adamantyl)-2,6-di-t-butyl-4-methyl-glycidyloxybenzene, 3,5-bis(1-adamantyl)-2-t-butyl-4-methyl-glycidyloxybenzene, 3,6-bis(1-adamantyl)-2-t-butyl-4-methyl-glycidyloxybenzene, 5,6-bis(1-adamantyl)-2-t-butyl-4-methyl-glycidyloxybenzene, 3,5,6-tris(1-adamantyl)-2-t-butyl-4-methyl-glycidyloxybenzene, 4,6-bis(1-adamantyl)-2,3,5-trimethyl-glycidyloxybenzene, 2,4-bis(1-adamantyl)-1,3-diglycidyloxybenzene, 2,5-bis(1-adamantyl)-1,3-diglycidyloxybenzene, 4,6-bis(1-adamantyl)-1,3-diglycidyloxybenzene, 4,5-bis(1-adamantyl)-1,3-diglycidyloxybenzene, 2,4,5-tris(1-adamantyl)-1,3-diglycidyloxybenzene, 2,4,6-tris(1-adamantyl)-1,3-diglycidyloxybenzene, 4,5,6-tris(1-adamantyl)-1,3-diglycidyloxybenzene, 2,4,5,6-tetrakis(1-adamantyl)-1,3-diglycidyloxybenzene, 3,4-bis(1-adamantyl)-1,2-diglycidyloxybenzene, 3,5-bis(1-adamantyl)-1,2-diglycidyloxybenzene, 3,6-bis(1-adamantyl)-1,2-diglycidyloxybenzene, 4,5-bis(1-adamantyl)-1,2-diglycidyloxybenzene, 3,4,5-tris(1-adamantyl)-1,2-diglycidyloxybenzene, 3,4,5,6-tetrakis(1-adamantyl)-1,2-diglycidyloxybenzene, 2,3-bis(1-adamantyl)-1,4-diglycidyloxybenzene, 2,5-bis(1-adamantyl)-1,4-diglycidyloxybenzene, 2,6-bis(1-adamantyl)-1,4-diglycidyloxybenzene, 2,3,5-tris(1-adamantyl)-1,4-diglycidyloxybenzene, 2,3,5,6-tetrakis(1-adamantyl)-1,4-diglycidyloxybenzene, 2,5-bis(1-adamantyl)-4-hexyl-1,3-diglycidyloxybenzene, 2,6-bis(1-adamantyl)-4-hexyl-1,3-diglycidyloxybenzene, 5,6-bis(1-adamantyl)-4-hexyl-1,3-diglycidyloxybenzene, 2,5,6-tris(1-adamantyl)-4-hexyl-1,3-diglycidyloxybenzene, 4,6-bis(1-adamantyl)-2,5-dimethyl-1,3-diglycidyloxybenzene, 4,5-bis(1-adamantyl)-2-methyl-1,3-diglycidyloxybenzene, 4,6-bis(1-adamantyl)-2-methyl-1,3-diglycidyloxybenzene, 4,5,6-tris(1-adamantyl)-2-methyl-1,3-diglycidyloxybenzene, 2,4-bis(1-adamantyl)-5-methyl-1,3-diglycidyloxybenzene, 4,6-bis(1-adamantyl)-5-methyl-1,3-diglycidyloxybenzene, 2,4-bis(1-adamantyl)-5-methyl-1,3-diglycidyloxybenzene, 4,6-bis(1-adamantyl)-3,5-di-t-butyl-1,2-diglycidyloxybenzene, 3,5-bis(1-adamantyl)-4-methyl-1,2-diglycidyloxybenzene, 3,6-bis(1-adamantyl)-4-methyl-1,2-diglycidyloxybenzene, 5,6-bis(1-adamantyl)-4-methyl-1,2-diglycidyloxybenzene, 3,5,6-tris(1-adamantyl)-4-methyl-1,2-diglycidyloxybenzene, 3,5-bis(1-adamantyl)-4-t-butyl-1,2-diglycidyloxybenzene, 3,6-bis(1-adamantyl)-4-t-butyl-1,2-diglycidyloxybenzene, 5,6-bis(1-adamantyl)-4-t-butyl-1,2-diglycidyloxybenzene, 3,5,6-tris(1-adamantyl)-4-t-butyl-1,2-diglycidyloxybenzene, 3,5-bis(1-adamantyl)-2-methyl-1,4-diglycidyloxybenzene, 3,6-bis(1-adamantyl)-2-methyl-1,4-diglycidyloxybenzene, 3,5,6-tris(1-adamantyl)-2-methyl-1,4-diglycidyloxybenzene, 3,5-bis(1-adamantyl)-2-t-butyl-1,4-diglycidyloxybenzene, 3,6-bis(1-adamantyl)-2-t-butyl-1,4-diglycidyloxybenzene, 3,5,6-tris(1-adamantyl)-2-t-butyl-1,4-diglycidyloxybenzene, 3,6-bis(1-adamantyl)-2,5-di-t-butyl-1,4-diglycidyloxybenzene, 4,5-bis(1-adamantyl)-1,2,3-triglycidyloxybenzene, 4,6-bis(1-adamantyl)-1,2,3-triglycidyloxybenzene, 4,5,6-tris(1-adamantyl)-1,2,3-triglycidyloxybenzene, 2,5-bis(1-adamantyl)-1,3,4-triglycidyloxybenzene, 2,6-bis(1-adamantyl)-1,3,4-triglycidyloxybenzene, 5,6-bis(1-adamantyl)-1,3,4-triglycidyloxybenzene, 2,5,6-tris(1-adamantyl)-1,3,4-triglycidyloxybenzene and the like.

The adamantyl group-containing epoxy modified acrylates represented by the above-mentioned general formula (III) can be obtained by reacting the glycidyloxy group-containing adamantane derivative represented by the above-mentioned general formula (II) with acrylic acids. In this acrylation reaction, the above-mentioned glycidyloxy group-containing adamantane derivative may be used alone or in a mixture of two or more kinds.

Examples of the acrylic acids used include acrylic acid, methacrylic acid, α-fluoroacrylic acid, and α-trifluoromethylacrylic acid. These acrylic acids may be used alone or in a mixture of two or more kinds.

The reaction between the above-mentioned glycidyloxy group-containing adamantane derivative and acrylic acids is usually carried out in the presence of a catalyst. Examples of the catalyst used include an organic amine such as triethylamine, tributylamine, pyridine, dimethylaminopyridine and the like; a quarternary ammonium salt such as tetramethylammonium chloride, tetramethylammonium bromide, tetraethylammonium chloride, tetraethylammonium bromide and the like; triphenylphosphine; and others. The amount of the catalyst to be used is usually approximately 0.01 to 20 mass %, preferably 0.05 to 15 mass %, relative to the acrylic acids.

The reaction is carried out in the absence or in the presence of a solvent. The solvent is advantageously selected so that the solubility of the above-mentioned glycidyloxy group-containing adamantane derivative is 0.5 mass % or more, desirably 5 mass % or more. In this reaction, although the above-mentioned glycidyloxy group-containing adamantane derivative may be reacted in a suspended state, it is desirable that the derivative is dissolved in the solvent. Specific examples of the solvent include cyclohexane, methylcyclohexane, ethylcyclohexane, toluene, xylene, MEK, MIBK (methyl isobutyl ketone), DMF (dimethylformamide), NMP (N-methyl-2-pyrrolidone), DMAc (N,N-dimethylacetamide), DMSO (dimethylsulfoxide), propyleneglycol monomethyl ether acetate and the like. These solvents may be used alone or in combination of two or more kinds.

The reaction of the glycidyloxy group-containing adamantane derivative and acrylic acids is usually carried out at a temperature of approximately 50 to 200° C., preferably 70 to 150° C. When the reaction temperature is 50° C. or higher, the reaction rate is not lowered and adequate, therefore, the reaction time is shortened. When the reaction temperature is 200° C. or lower, side reaction is suppressed and discoloration of the product is suppressed. The reaction pressure is approximately 0.01 to 10 MPa, desirably normal pressure to 1 MPa in absolute pressure. When the pressure is 10 MPa or less, the safety is secured and special equipment is not required, therefore this method is industrially useful. The reaction time is usually approximately 1 minute to 24 hours, desirably 1 to 10 hours.

In the reaction, a polymerization inhibitor such as hydroquinone, methoquinone, phenothiazine, methoxyphenothiazine and the like may be added as needed. The ratio of the polymerization inhibitor to be used is usually approximately 10 to 10,000 mass ppm, preferably 50 to 5,000 mass ppm, to the acrylic acids.

The reaction product is purified by distillation, crystallization, column separation, and the like. The method of purification may be selected according to the characteristics of the reaction product and the kind of the impurities.

Examples of the adamantyl group-containing epoxy modified acrylates represented by the above-mentioned general formula (III) thus obtained may include the compounds as exemplified by the glycidyloxy group-containing adamantane derivative represented by the above-mentioned general formula (II) in which "glycidyloxybenezene" is replaced by "-[(2-acryloyloxy-2-hydroxy)ethoxy]benzene", "-[(2-methacryloyloxy-2-hydroxy)ethoxy]benzene", "-[(2-α-fluoroacryloyloxy-2-hydroxy)ethoxy]benzene", and "-[(2-α-trifluoromethylacryloyloxy-2-hydroxy)ethoxy]benzene".

The resin composition (1) of the present invention contains the glycidyloxy group-containing adamantane derivative represented by the above-mentioned general formula (II) and an epoxy resin curing agent. In the resin composition (1) of the present invention, a mixture of the glycidyloxy group-containing adamantane derivative represented by the above-mentioned general formula (II) and other known epoxy resins may also be used in order to optimize the mechanical strength of the cured product and the solubility, workability, and the like of the resin composition.

Examples of the known epoxy resins include glycidyl ether type epoxy resin such as bisphenol-A type epoxy resin, bisphenol-F type epoxy resin, bisphenol-S type epoxy resin, bisphenol-AD type epoxy resin, hydrogenated bisphenol-A type epoxy resin, bisphenol-G type epoxy resin, tetramethylbisphenol-A type epoxy resin, fluorine-containing epoxy resin such as bisphenol-AF type epoxy resin, bisphenol-C type epoxy resin and the like; novolac type epoxy resin such as phenol-novolac type epoxy resin, cresol-novolac type epoxy resin and the like; alicyclic epoxy resin; azacyclic epoxy resin such as triglycidyl isocyanurate, hydantoin epoxy resin and the like; aliphatic epoxy resin; biphenyl type epoxy resin and dicyclo ring type epoxy resin as the mainstream of low water absorption cured product type; naphthalene type epoxy resin; multifunctional epoxy resin such as trimethylolpropane polyglycidyl ether, glycerol polyglycidyl ether, pentaerythritol polyglycidyl ether and the like; and others. These epoxy resins may be used alone or in combination of two or more kinds.

The above-mentioned known epoxy resins may be either solid or liquid at ordinary temperature, but in general, it is preferable that the average epoxy equivalent of the epoxy resin to be used is 100 to 2,000. When the epoxy equivalent is 100 or more, the cured product of the composition of the present invention does not become brittle and an adequate strength is obtained. In addition, when the epoxy equivalent is 2,000 or less, the glass transition temperature (Tg) of the cured product does not become lower and an adequate Tg is obtained.

The content of the above-mentioned glycidyloxy group-containing adamantane derivative in the mixture of the above-mentioned glycidyloxy group-containing adamantane derivative and the above-mentioned known epoxy resin is preferably 5 mass % or more, more preferably 10 mass % or more. When the content of the glycidyloxy group-containing adamantane derivative is 5 mass % or more, the optical characteristics, long-term heat resistance, and electric characteristics of the resin composition of the present invention are sufficient.

As an epoxy resin curing agent contained in the resin composition (1) of the present invention, at least one kind selected from a cationic polymerization initiator, an acid anhydride curing agent, an amine curing agent, a phenolic curing agent, and the like is mentioned. That is, the resin composition (1) of the present invention is cured by a reaction using such an epoxy resin curing agent.

As the cationic polymerization initiator, one which reacts with an epoxy ring by heat or an ultraviolet light may be used. The examples include an aromatic diazonium salt such as p-methoxybenzenediazonium hexafluorophosphate and the like, an aromatic sulfonium salt such as triphenylsulfonium hexaflurophosphate and the like, an aromatic iodonium salt such as diphenyliodonium hexafluorophosphate and the like, an aromatic iodosyl salt, an aromatic sulfoxonium salt, metallocene compound and the like. Among these, an aromatic sulfonium salt such as triphenylsulfonium hexafluorophosphate and the like and an aromatic iodonium salt such as diphenyliodonium hexafluorophosphate and the like are most suitable. These initiators may be used alone or in combination of two or more kinds.

The amount of the cationic polymerization initiator to be used is preferably 0.01 to 5.0 parts by mass, more preferably 0.1 to 3.0 parts by mass, relative to 100 parts by mass of the above-mentioned glycidyloxy group-containing adamantane derivative or the above-mentioned mixed resin (hereinafter, optionally referred to as "resin component"). By setting the content of the cationic initiator in the above-mentioned range, good polymerization characteristics and physical properties such as optical characteristics and the like can be expressed.

Examples of the acid anhydride curing agent include phthalic anhydride, maleic anhydride, trimellitic anhydride, pyromellitic anhydride, hexahydrophthalic anhydride, tetrahydrophthalic anhydride, methylnadic anhydride, nadic anhydride, glutaric anhydride, methylhexahydrophthalic anhydride, methyltetrahydrophthalic anhydride and the like. Among these, hexahydrophthalic anhydride, tetrahydrophthalic anhydride, methylhexahydrophthalic anhydride, and methyltetrahydrophthalic anhydride are most suitable. These anhydrides may be used alone or in combination of two or more kinds.

When the acid anhydride curing agent is used, a curing accelerator may be blended in order to accelerate the curing. Examples of the curing accelerator include tertiary amines, imidazoles, organic phosphine compounds, or salts of them, and metal soaps such as zinc octylate, tin octylate and the like. These curing accelerators may be used alone or in combination of two or more kinds.

Examples of the phenolic curing agent include phenol novolac resin, cresol novolac resin, bisphenol-A novolac resin, triazine modified phenol novolac resin and the like. Examples of the amine curing agent include dicyandiamide; aromatic diamine such as m-phenylenediamine, 4,4'-diaminodiphenylmethane, 4,4'-diaminodiphenylsulfone, m-xylylenediamine and the like; and others. These curing agents may be used alone or in combination of two or more kinds.

Among these curing agents, acid anhydride curing agents are suitable from a viewpoint of a physical property such as transparency and the like of the cured resin. Among these, hexahydrophthalic anhydride, tetrahydrophthalic anhydride, methylhexahydrophthalic anhydride, and methyltetrahydrophthalic anhydride are most suitable.

The ratio of the resin component and the curing agent is determined by the ratio of the glycidyl group and the functional group of the reacting curing agent. Usually, the ratio of the number of the corresponding functional group of the curing agent to the number of the glycidyl group is 0.5 to 1.5, preferably 0.7 to 1.3. By setting the ratio of the resin component and the curing agent in the above-mentioned range, the curing rate of the composition is not slowed, the glass transition temperature of the cured resin is not lowered, and further the moisture resistance is not decreased, therefore the range is suitable.

In the present invention, by reacting the adamantane derivative of the present invention, which is excellent in heat resistance and transparency, with the above-mentioned curing agent, not only the heat resistance and transparency but also the light resistance, and further dielectric constant and the like are improved. In addition, solubility which is required practically is imparted.

Furthermore, to the resin composition (1) of the present invention, various known additives which are conventionally used, such as a curing accelerator, an anti-deterioration agent, a modifying agent, a silane coupling agent, a defoaming agent, inorganic powders, a solvent, a leveling agent, a mold release agent, dye, pigment and the like may be appropriately blended as needed.

The above-mentioned curing accelerator is not particularly limited. The examples include 1,8-diaza-bicyclo[5.4.0]undecene-7, triethylenediamine, tertiary amines such as tris(2,4,6-dimethylaminomethyl)phenol and the like; imidazoles such as 2-ethyl-4-methylimidazole, 2-methylimidazole and the like; phosphorus compounds such as triphenylphosphine, tetraphenylphosphonium bromide, tetraphenylphosphonium tetraphenylborate, tetra-n-butylphosphonium-O,O-diethylphosphorodithioate and the like; quarternary ammonium salts; organic metal salts; derivatives of them; and others. These curing accelerators may be used alone or in combination. Among these curing accelerators, it is preferable to use tertiary amines, imidazoles, and phosphorus compounds.

The content of the curing accelerator is preferably 0.01 to 8.0 parts by mass, more preferably 0.1 to 3.0 parts by mass, relative to 100 parts by mass of the above-mentioned resin component. By setting the content of the curing accelerator in the above-mentioned range, sufficient curing acceleration effect is attained and there is no discoloration in the cured product obtained.

Examples of the anti-deterioration agent include conventionally known anti-deterioration agents such as phenolic compounds, amine compounds, organic sulfur compounds, phosphorus compounds and the like. By adding the anti-deterioration agent, characteristics of the resin composition (1) of the present invention such as heat resistance, transparency and the like are retained.

Examples of the phenolic compounds include commercially available products such as Irganox 1010 (Chiba Specialty Chemicals, trade mark), Irganox 1076 (Chiba Specialty Chemicals, trade mark), Irganox 1330 (Chiba Specialty Chemicals, trade mark), Irganox 3114 (Chiba Specialty Chemicals, trade mark), Irganox 3125 (Chiba Specialty Chemicals, trade mark), Irganox 3790 (Chiba Specialty Chemicals, trade mark), BHT, Cyanox 1790 (Cyanamid, trade mark), Sumilizer GA-80 (Sumitomo Chemical Co., Ltd., trade mark) and the like.

Examples of the amine compound include IRGASTAB FS 042 (Chiba Specialty Chemicals, trade mark), GENOX EP (Crompton Corporation, trade mark, compound name: dialkyl-N-methylamine oxide) and the like, as well as hindered amine such as ADK STAB LA-52, LA-57, LA-62, LA-63, LA-67, LA-68, LA-77, LA-82, LA-87 and LA-94 (Adeka Corporation), Tinuvin 123, 144, 440 and 662, and Chimassorb 2020, 119 and 944 (CSC), Hostavin N30 (Hoechst), Cyasorb UV-3346 and UV-3526 (Cytec Industries Inc.), Uval 299 (GLC), Sanduvor PR-31 (Clariant) and the like.

Examples of the organic sulfur compound include commercial products such as DSTP (Yoshitomi) (Yoshitomi Fine Chemicals, trade mark), DLTP (Yoshitomi) (Yoshitomi Fine Chemicals, trade mark), DLTOIB (Yoshitomi Fine Chemicals, trade mark), DMTP (Yoshitomi) (Yoshitomi Fine Chemicals, trade mark), Seenox 412S (SHIPRO KASEI KAISHA, LTD., trade mark), Cyanox 1212 (Cyanamid, trade mark) and the like.

As a modifying agent, conventional known modifying agents such as glycols, silicones, alcohols and the like may be mentioned. As a silane coupling agent, conventional known silane coupling agents such as silanes, titanates and the like may be mentioned. As a defoaming agent, conventional known defoaming agents such as silicones and the like may be mentioned. As inorganic powders, the ones having a particle diameter of several nm to 10 μm may be used depending on the intended use. The examples include known inorganic powders such as glass powders, silica powders, titania, zinc oxide, alumina and the like. As a solvent, an aromatic solvent such as toluene, xylene and the like and a ketone solvent such as methyl ethyl ketone, methyl isobutyl ketone, cyclohexanone and the like may be used as a diluent for a powdery resin component or a coating agent.

As a curing method of the resin composition (1) of the present invention, for example, a method of mixing the above-mentioned resin component and the epoxy resin curing agent with various additives, configuring into a desired shape by injecting the mixture into a molding die (resin die) or by coating, and curing by heating or the ultraviolet irradiation may be used. In the case of heat curing, the curing temperature is usually approximately 50 to 200° C., preferably 100 to 180° C. By setting the curing temperature at 50° C. or higher, incomplete curing is avoided. By setting the curing temperature at 200° C. or lower, discoloration is avoided. Although the curing time varies depending on the resin component, curing agent, accelerator, and initiator to be used, it is preferably 0.5 to 6 hours.

Irradiation intensity of the ultraviolet light is usually approximately 500 to 5,000 mJ/cm$^2$, preferably 1,000 to 4,000 mJ/cm$^2$. Post-heating may be carried out after the ultraviolet irradiation, preferably at 70 to 200° C. for 0.5 to 12 hours.

The molding method is not particularly limited and injection molding, blow molding, press molding and the like may be used, and the cured product is preferably produced by injection-molding the composition in a pellet form using an injection molding machine.

The cured product obtained by curing the resin composition (1) of the present invention is excellent in heat resistance and transparency, and may attain the total light transmittance as high as 70% or more. As shown in Examples later, the cured product that is excellent in workability because of its low dissolution temperature, has a high glass transition temperature, excellent durability (heat resistance and light resistance), and is excellent in electric characteristics such as dielectric constant and the like is obtained.

Thus, since the resin composition (1) of the present invention has excellent characteristics, it may be suitably used for an optoelectronic part such as a resin (sealant and adhesive) for an optical semiconductor (LED and the like), a flat panel display (organic EL element and the like), an electronic circuit, and an optical circuit (optical waveguide), a lens for optical communication, an optical film, and the like.

Therefore, the resin composition (1) of the present invention is used as a semiconductor element and/or an integrated circuit (IC and the like) and individual semiconductors (diode, transistor, thermistor, and the like), for LED (an LED lamp, chip LED, a light receiving element, and a lens for an optical semiconductor), a sensor (a temperature sensor, an optical sensor, and a magnetic sensor), a passive part (a high frequency device, a resistor, a condenser and the like), an electromechanical part (a connector, a switch, a relay and the like), an automobile part (a circuit system, a control system, sensors, a lamp seal and the like), and an adhesive (optical parts, an optical disc, and a pickup lens), and others, as well as for an optical film as a surface coating agent, and the like.

The composition as a sealant for an optical semiconductor (LED and the like) may be applied to an element such as bombshell type LED, surface mount type (SMT) LED or the like. The composition satisfactorily adheres to a semiconductor made of GaN and the like formed on a metal or polyamide. The composition may also be used with a fluorescent dye such as YAG and the like dispersed. Furthermore, the composition is applicable as a surface coating agent for bombshell type LED, a lens for SMT type LED and the like.

When applied to the organic EL, the composition is applicable to an organic EL element having layers of a positive electrode, a hole-injecting layer, a luminescent layer, an electron-injecting layer, and a negative electrode in this order on a light-transmitting substrate such as commonly-used glass, transparent resin and the like. As for a sealant of an organic EL element, it may directly seal the EL element by using the composition as an adhesive to cover the EL element with a metal can, a metal foil, or a resin film coated with SiN and the like. Alternatively, the EL element may be directly sealed by the glycidyloxy group-containing adamantane derivative of the present invention with an inorganic filler and the like dispersed in order to impart the gas barrier property to the glycidyloxy group-containing adamantane derivative. As for the display method, although the composition is applicable to the bottom emission system which is currently mainstream, the effect of the transparency and heat resistance of the glycidyloxy group-containing adamantane derivative of the present invention may be utilized by applying the composition to the top emission system which is prospective in light extraction efficiency and the like in the future.

When applied to the electronic circuit, the resin composition is applicable as an interlayer insulation film, an adhesive between the polyimide for the flexible print board and copper foil, or a resin for a substrate board.

When applied to the optical circuit, the resin composition is also applicable to a thermooptical switch for single and multi modes, an arrayed waveguide grating, a multi/demultiplexer, a wavelength variable filter, or a core or clad material of optical fiber. In addition, the resin composition is also applicable to a microlens array to condense light to the waveguide and a mirror of MEMS type optical switch. Furthermore, the resin composition is also applicable to a dye binder of a photoelectric conversion element.

When used as the optical film, the resin composition is applicable to display such as a film board for liquid crystal, a film board for organic EL, and the like, as well as a light diffusion film, an antireflection film, a color conversion film with a fluorescent dye and the like dispersed, and others.

The resin composition (2) of the present invention contains the adamantyl group-containing epoxy modified (meth)acrylate represented by the above-mentioned general formula (III) and a thermopolymerization initiator or a photopolymerization initiator. In the resin composition (2) of the present invention, a mixed resin of the above-mentioned adamantyl group-containing epoxy modified acrylates and another polymerizable monomer may be used as long as it does not adversely affect the transparency, heat resistance, and the like. Examples of other polymerizable monomer include methyl (meth)acrylate, ethyl (meth)acrylate, propyl (meth)acrylate, butyl (meth)acrylate, cyclohexyl (meth)acrylate, dicyclopentanyl (meth)acrylate, 1-adamantyl (meth)acrylate, ethyleneglycol di(meth)acrylate, 1,3-propanediol di(meth)acrylate, 1,4-butanediol di(meth)acrylate, pentaerythritol tri(meth)acrylate, pentaerythritol tetra(meth)acrylate, dipentaerythritol penta(meth)acrylate, dipentaerythritol hexa(meth)acrylate, trimethylolpropane tri(meth)acrylate, ditrimethylolpropane tetra(meth)acrylate, adamantanediol di(meth)acrylate, adamantanedimethanol di(meth)acrylate, adamantanediethanol di(meth)acrylate and the like. These monomers may be used alone or in combination of two or more kinds.

In addition, in the resin composition (2) of the present invention, a mixture of the adamantyl group-containing epoxy modified acrylates represented by the above-mentioned general formula (III) and an epoxy (meth)acrylate obtained by a reaction of the known epoxy resin exemplified in the above-mentioned resin composition (1) and (meth)acrylic acid may be used.

In the mixed resin of the adamantyl group-containing epoxy modified acrylates represented by the above-mentioned general formula (III) and the above-mentioned other polymerizable monomer and/or epoxy resin modified (meth)acrylate, the content of the above-mentioned adamantyl group-containing epoxy modified acrylates is preferably 5 mass % or more, more preferably 10 mass % or more. When the content of the adamantyl group-containing epoxy modified acrylates is 5 mass % or more, the optical characteristics, long term heat resistance, and electric characteristics of the resin composition (2) of the present invention are sufficient.

The resin composition (2) of the present invention is cured by polymerization using a thermopolymerization initiator or a photopolymerization initiator. As the thermopolymerization initiator, one which reacts with a group having an unsaturated bond, that is, an acryloyl group or a methacryloyl group by heat may be used. The examples include an organic peroxide such as benzoyl peroxide, methyl ethyl ketone peroxide, methyl isobutyl ketone peroxide, cumene hydroperoxide, t-butyl hydroperoxide and the like, an azo initiator such as azobisisobutyronitrile and the like, and others. These initiators may be used alone or in combination of two or more kinds.

As the photopolymerization initiator, one which reacts with a group having an unsaturated bond, that is, an acryloyl group or a mathacryloyl group by light irradiation may be used. The examples include acetophenones, benzophenones, benzils, benzoin ethers, benzil diketals, thioxanthones, acylphosphine oxides, acylphosphinic acid esters, aromatic diazonium salts, aromatic sulfonium salts, aromatic iodonium salts, aromatic iodosyl salts, aromatic sulfoxonium salts, metallocene compounds, and the like. These initiators may be used alone or in combination of two or more kinds.

The amount of the thermopolymerization initiator or photopolymerization initiator to be used is preferably 0.01 to 10 parts by mass, more preferably 0.05 to 5 parts by mass, relative to 100 parts by mass of the above-mentioned adamantyl group-containing epoxy modified acrylates or the above-mentioned mixed resin (hereinafter, sometimes referred to as "resin component"). By setting the content of the polymerization initiator in the above-mentioned range, good polymerization characteristics and physical properties such as optical characteristics and the like are expressed.

The resin composition (2) of the present invention may be added with various known additives which are conventionally used, such as an anti-deterioration agent, a modifying agent, a silane coupling agent, a defoaming agent, inorganic powder, a solvent, a leveling agent, a mold release agent, dye, pigment and the like, as needed. Specific examples of the anti-deterioration agent and the like are similar to those exemplified in the above-mentioned resin composition (1).

The resin composition (2) of the present invention is photocured by mixing the above-mentioned resin component, a thermopolymerization initiator or a photopolymerization initiator, and various additives, configuring into a desired shape by injecting the mixture into a molding die (resin die) or by coating, and heating or irradiating with an ultraviolet light and the like. In the case of heat curing, the curing temperature is usually approximately 30 to 200° C., preferably 50 to 150° C. By setting the curing temperature at 30° C. or higher, incomplete curing is avoided. By setting the curing temperature at 200° C. or lower, discoloration and the like are avoided. Although the curing time varies depending on the resin component, polymerization initiator and the like to be used, it is preferably 0.5 to 6 hours.

In the case of photocuring by the ultraviolet irradiation, although the irradiation intensity of the ultraviolet light is optionally determined by the kind of the resin component and the polymerization initiator, film thickness of the cured product, and the like, it is usually approximately 100 to 5,000 mJ/cm$^2$, preferably 500 to 4,000 mJ/cm$^2$. Post-heating may be carried out after the ultraviolet irradiation, preferably at 70 to 200° C. for 0.5 to 12 hours.

The molding method is not particularly limited and injection molding, blow molding, press molding and the like may be used, and the cured product is preferably produced by injection-molding the resin composition in a pellet form using an injection molding machine.

The cured product obtained by curing the resin composition (2) of the present invention is excellent in transparency, heat resistance, and mechanical properties such as hardness and the like, and may be advantageously used as a solder resist for an interconnection substrate, a protection film for a color filter of a liquid crystal display and an image sensor, a colored composition for a color filter, a sealant for an electronic circuit (a sealant for an optical semiconductor and a sealant for an organic EL element), an optoelectronic part (an optical waveguide, a lens for optical communication, an optical film, and the like), and adhesives for these devices, and others.

Furthermore, the resin composition (2) of the present invention is used as a semiconductor element and/or an integrated circuit (IC and the like) and individual semiconductors (diode, transistor, thermistor, and the like), for LED (an LED lamp, chip LED, a light receiving element, and a lens for an optical semiconductor), a sensor (a temperature sensor, an optical sensor, and a magnetic sensor), a passive part (such as a high frequency device, a resistor, a condenser and the like), an electromechanical part (such as a connector, a switch, a relay and the like), an automobile part (such as a circuit system, a control system, sensors, a lamp seal and the like), an adhesive (an optical part, an optical disc, and a pickup lens), and others, as well as for an optical film and the like as a surface coating agent.

EXAMPLES

Hereinafter the present invention is explained in more detail by Examples. The present invention is not at all limited by these Examples. In the following Examples and Comparative Examples, the obtained composition and the like were evaluated as follows.

(1) Glass Transition Temperature

Glass transition temperature was defined as a discontinuous point observed on a heat flux curve obtained by raising the temperature of 10 mg of a sample at a rate of 10° C./min after keeping the sample at 50° C. for 5 minutes under nitrogen atmosphere, using a differential scanning calorimeter (DSC-7 manufactured by PerkinElmer Inc.).

(2) Light Transmittance

Light transmittance was measured according to JIS K7105 using a sample piece of 3 mm thick at a measurement wavelength of 400 nm (unit: %). A spectrophotometer UV-3100S manufactured by Shimadzu Corporation was used as the measurement apparatus.

(3) Light Resistance Test

The sample was irradiated with a light at 60° C. for 500 hours using SUNTEST CPS+ manufactured by Toyo Seiki Seisaku-sho, Ltd. and the change of the light transmittance at 400 nm before and after the irradiation was measured using a sunshine tester. When the rate of decrease of the light transmittance is less than 20%, the evaluation is "good". When the rate of decrease is 20% or more, the evaluation is "poor".

(4) Long Term Heat Resistance Test

The sample was placed in a constant temperature bath at 140° C. for 100 hours and the change of the light transmittance at 400 nm before and after the testing was measured using a sunshine tester. When the light transmittance decreased 20% or more, the evaluation is "poor".

Example 1

Synthesis of 4,6-bis(1-adamantyl)-1,3-dihydroxybenzene

A 500 mL four-necked flask equipped with a reflux condenser, a stirrer, a thermometer, and a nitrogen inlet tube was charged with 28.1 g (0.18 mol) of 1-adamantanol, 15.84 g (0.09 mol) of p-toluenesulfonic acid monohydrate, and 300 mL of heptane and replaced with nitrogen. The mixture was added with 9.9 g (0.09 mol) of resorcinol. The flask was immersed in an oil bath at 100° C. and the mixture was heated while stirring for 1 hour. After cooling the reaction mixture, the solid content was collected by filtration, which was then dried under vacuum, followed by recrystallization by aqueous methanol solution to obtain 4,6-bis(1-adamantyl)-1,3-dihydroxybenzene (yield: 86%, LC (liquid chromatography) purity: 99.7%, melting point: 146° C.). Note that the LC purity was measured by absorbance at $\lambda$=280 nm.

The obtained 4,6-bis(1-adamantyl)-1,3-dihydroxybenzene, was identified by nuclear magnetic resonance spectrum ($^1$H-NMR and $^{13}$C-NMR). The spectrum data are shown below. The nuclear magnetic resonance spectrum was measured using chloroform-d as a solvent and JNM-ECA500 manufactured by JEOL Ltd. as a measurement apparatus.

¹H-NMR (500 MHz): 1.68-1.82 (18H), 2.07 (d, 12H), 6.70 (d, 1H), 6.77 (d, 1H)

¹³C-NMR (125 MHz): 29.2, 36.0, 36.9, 40.7, 43.6, 109.9, 115.4, 136.0, 141.4

Example 2

Synthesis of 4,6-bis(1-adamantyl)-1,3-diglycidyloxybenzene

A 500 mL four-necked flask equipped with a reflux condenser, a stirrer, a thermometer, and a nitrogen inlet tube was charged with 57 mL of MIBK, 157 mL of DMSO, and 98 g (1.057 mol) of epichlorohydrin and replaced with nitrogen for 30 minutes. To this solution, 52.01 g (0.137 mol) of 4,6-bis(1-adamantyl)-1,3-dihydroxybenzene synthesized in Example 1 was added, and the flask was replaced with nitrogen for 30 minutes and then heated at 45° C. while stirring. This solution was added with 11.6 g (0.290 mol) of sodium hydroxide over 0.5 hour and the solution was stirred for 1.5 hours. Then, 2.9 g (0.0725 mol) of sodium hydroxide was added and the solution was further stirred for 1 hour. The reaction mixture was cooled to room temperature, and 300 mL of chloroform was added. After washing with 500 mL of water, an aqueous 0.1 mol/L HCl solution was added to the mixture and the organic layer was separated. After further washing with water until the aqueous phase became neutral, the organic layer was concentrated and dried until the weight became constant in a reduced pressure drier at 100° C. to obtain 4,6-bis(1-adamantyl)-1,3-diglycidyloxybenzene as a pale-yellow solid (yield: 92%, LC purity: 99.20%, epoxy equivalent: 267, melting point: 193° C.).

The obtained 4,6-bis(1-adamantyl)-1,3-diglycidyloxybenzene, was identified by nuclear magnetic resonance spectrum (¹H-NMR and ¹³C-NMR). The spectrum data are shown below. The nuclear magnetic resonance spectrum was measured using chloroform-d as a solvent and JNM-ECA500 manufactured by JEOL Ltd. as a measurement apparatus.

¹H-NMR (500 MHz): 1.77 (s, 12H), 2.08 (s, 20H), 2.80 (dd, 2H), 2.91 (dd, 1H), 3.39 (m, 2H), 3.98 (dd, 2H), 4.24 (dd, 2H), 6.47 (s, 1H), 7.08 (s, 1H)

¹³C-NMR (125 MHz): 29.2, 36.7, 37.2, 41.1, 44.7, 50.5, 69.0, 99.6, 125.0, 130.5, 155.9

Example 3

5 g of 4,6-bis(1-adamantyl)-1,3-diglycidyloxybenzene obtained in Example 2, 3.06 g of methylhexahydrophthalic anhydride (MH700 manufactured by New Japan Chemical Co., Ltd.) as an acid anhydride, and 0.1 g of octylic acid salt of 1,8-diazabicyclo[5.4.0]undecene-7 (SA102 manufactured by San-Apro Ltd.) as a curing accelerator were mixed at room temperature and, after defoaming, the mixture was heated at 110° C. for 2 hours and then at 170° C. for 4 hours to produce the cured resin (a sheet of 3 mm thickness). The glass transition temperature and light transmittance of the obtained cured resin product were measured, and further the light resistance test and long term heat resistance test were carried out. The evaluation results are shown in Table 1.

Example 4

2.5 g of 4,6-bis(1-adamantyl)-1,3-diglycidyloxybenzene obtained in Example 2, 2.5 g of bisphenol-A type epoxy resin (Epikote 828 manufactured by Japan Epoxy Resins Co., Ltd.), 3.73 g of methylhexahydrophthalic anhydride (MH700 manufactured by New Japan Chemical Co., Ltd.) as an acid anhydride, and 0.1 g of octylic acid salt of 1,8-diazabicyclo[5.4.0]undecene-7 (SA102 manufactured by San-Apro Ltd.) as a curing accelerator were mixed at room temperature and, after defoaming, the mixture was heated at 110° C. for 2 hours and then at 170° C. for 4 hours to produce the cured resin (a sheet of 3 mm thickness). The obtained cured resin product was evaluated similarly to those in Example 1. The evaluation results are shown in Table 1.

Comparative Example 1

Except for bisphenol-A type epoxy resin (Epikote 828 manufactured by Japan Epoxy Resins Co., Ltd.) was used instead of 4,6-bis(1-adamantyl)-1,3-diglycidyloxybenzene in Example 3 and 4.40 g of methylhexahydrophthalic anhydride was used, the cured resin was produced by a similar method to that in Example 1 and evaluated similarly. The evaluation results are shown in Table 1.

TABLE 1

|  | Example 3 | Example 4 | Comparative Example 1 |
|---|---|---|---|
| Glass transition temperature (° C.) | 221 | 186 | 140 |
| Light transmittance (%) | 86 | 83 | 80 |
| Light resistance | Good | Good | Poor |
| Heat resistance | Good | Good | Good |

Example 5

Synthesis of Adamantyl Group-Containing Epoxy Modified Acrylate

A 300 mL separable flask equipped with a reflux condenser, a stirrer, a thermometer, and an air inlet tube was charged with 18.8 g of 4,6-bis(1-adamantyl)-1,3-diglycidyloxybenzene obtained in Example 2, 6.1 g of acrylic acid, 50 mL of toluene, 0.61 g of tetraethylammonium bromide, and 6.1 mg of p-methoxyphenol. The mixture was heated to 120° C. under an air stream of a low flow rate and stirred for 20 hours. Then, 80 mL of toluene was added to the reaction mixture, which was cooled to room temperature. The toluene solution was washed twice with aqueous 5 mass % sodium chloride solution and once with pure water, followed by concentrating the organic layer to obtain 23.2 g of adamantyl group-containing epoxy modified acrylate represented by the following formula (LC purity: 91%).

[Chemical formula 10]

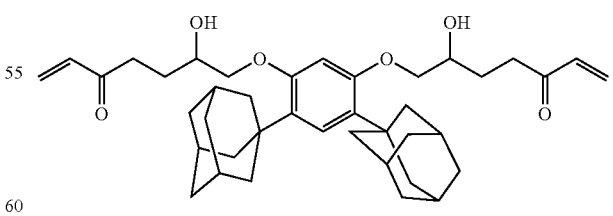

The adamantyl group-containing epoxy modified acrylate was identified by nuclear magnetic resonance spectrum (¹H-NMR and ¹³C-NMR). The spectrum data are shown below. The nuclear magnetic resonance spectrum was measured using chloroform-d as a solvent and JNM-ECA500 manufactured by JEOL Ltd. as a measurement apparatus.

$^1$H-NMR (500 MHz): 1.75 (s, 12H), 2.07 (s, 20H), 3.98-4.49 (m, 10H), 5.88 (d, 2H), 6.15 (dd, 2H), 6.45 (d, 2H), 7.10 (s, 1H), 7.25 (s, 1H)
$^{13}$C-NMR (125 MHz): 29.1, 36.7, 37.1, 41.3, 65.9, 66.0, 68.9, 98.9, 125.3, 127.8, 130.4, 131.7, 155.7, 166.4

Example 6

10 g of epoxy modified acrylate obtained in Example 5 and 0.1 g of benzoin isobutyl ether as a photopolymerization initiator was mixed to prepare a resin composition, the obtained resin composition was applied on a glass substrate so that the applied thickness is 0.1 mm and irradiated with a high pressure mercury lamp to cure. The glass transition temperature of the obtained cured product was as high as 184° C.

INDUSTRIAL APPLICABILITY

The adamantane derivative of the present invention provides a cured product excellent in optical characteristics such as transparency, (long term) light resistance and the like, (long term) heat resistance, and mechanical properties, and is suitable as a solder resist for an interconnection substrate, a protection film for a color filter of a liquid crystal display and an image sensor, a colored composition for a color filter, a sealant for an electronic circuit (a sealant for an optical semiconductor and a sealant for an organic EL element), an optoelectronic part (an optical waveguide, a lens for optical communication, an optical film, and the like), adhesives for these devices, and others.

The invention claimed is:

1. An adamantane derivative represented by the following general formula (II):

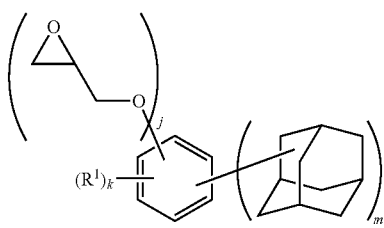

(II)

wherein:
R$^1$ represents C$_n$H$_{2n+1}$ and n is an integer of 1 to 10;
j is an integer of 1 to 4;
k is an integer of 0 to 3;
m is an integer of 2 to 5; and
j+k+m≦6.

2. A method for producing an adamantane derivative represented by the following general formula (II), wherein the method comprises reacting an adamantane derivative represented by the following general formula (I) with epichlorohydrin:

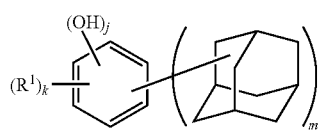

(I)

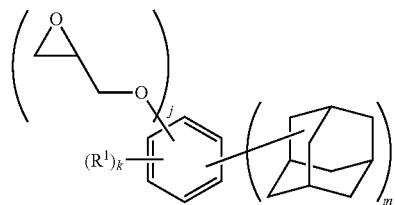

(II)

wherein:
R$^1$ represents C$_n$H$_{2n+1}$ and n is an integer of 1 to 10;
j is an integer of 1 to 4;
k is an integer of 0 to 3;
m is an integer of 2 to 5; and
j+k+m≦6.

3. A resin composition comprising: the adamantane derivative represented by the general formula (II) according to claim 1; and an epoxy resin curing agent.

4. A cured product obtained by curing the resin composition according to claim 3 by heating or light irradiation.

5. An adamantane derivative represented by the following general formula (III):

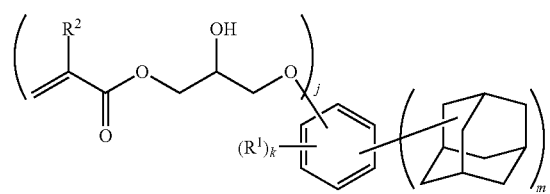

(III)

wherein:
R$^1$ represents C$_n$H$_{2n+1}$ and n is an integer of 1 to 10;
R$^2$ represents H, CH$_3$, F, or CF$_3$;
j is an integer of 1 to 4;
k is an integer of 0 to 3;
m is an integer of 2 to 5; and
j+k+m≦6.

6. A method for producing an adamantane derivative represented by the following general formula (III), wherein the method comprises reacting an adamantane derivative represented by the following general formula (II) with an acrylic acid:

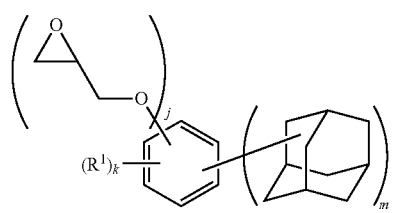

(II)

-continued

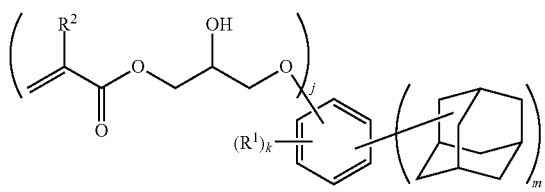

(III)

wherein:
$R^1$ represents $C_nH_{2n+1}$ and n is an integer of 1 to 10;
$R^2$ represents H, $CH_3$, F, or $CF_3$;
j is an integer of 1 to 4;
k is an integer of 0 to 3;
m is an integer of 2 to 5; and
$j+k+m \leq 6$.

7. A resin composition comprising: the adamantane derivative represented by the general formula (III) according to claim 5; and a thermopolymerization initiator or a photopolymerization initiator.

8. A cured product obtained by curing the resin composition according to claim 7 by heating or light irradiation.

9. 4,6-bis(1-adamantyl)-1,3-diglycidyloxybenzene.

10. A method for producing the 4,6-bis(1-adamantyl)-1,3-diglycidyloxybenzene according to claim 9, wherein the method comprises reacting 4,6-bis(1-adamantyl)-1,3-dihydroxybenzene with epichlorohydrin.

11. A resin composition comprising: the 4,6-bis(1-adamantyl)-1,3-diglycidyloxybenzene according to claim 9; and an epoxy resin curing agent.

12. A cured product obtained by curing the resin composition according to claim 11 by heating or light irradiation.

* * * * *